United States Patent
Putman et al.

(10) Patent No.: US 10,518,480 B2
(45) Date of Patent: Dec. 31, 2019

(54) SYSTEMS, METHODS, AND MEDIA FOR ARTIFICIAL INTELLIGENCE FEEDBACK CONTROL IN ADDITIVE MANUFACTURING

(71) Applicant: Nanotronics Imaging, Inc., Cuyahoga Falls, OH (US)

(72) Inventors: Matthew C. Putman, Brooklyn, NY (US); Vadim Pinskiy, Wayne, NJ (US); James Williams, III, New York, NY (US); Damas Limoge, New York, NY (US); Aswin Raghav Nirmaleswaran, Brooklyn, NY (US); Mario Chris, Brooklyn, NY (US)

(73) Assignee: Nanotronics Imaging, Inc., Cuyahoga Falls, OH (US)

( * ) Notice: Subject to any disclaimer, the term of this patent is extended or adjusted under 35 U.S.C. 154(b) by 0 days.

(21) Appl. No.: 15/943,442

(22) Filed: Apr. 2, 2018

(65) Prior Publication Data
US 2019/0299536 A1   Oct. 3, 2019

(51) Int. Cl.
| | |
|---|---|
| B29C 64/393 | (2017.01) |
| B29C 64/209 | (2017.01) |
| B33Y 10/00 | (2015.01) |
| G06K 9/62 | (2006.01) |
| G06N 3/04 | (2006.01) |
| B33Y 50/02 | (2015.01) |

(52) U.S. Cl.
CPC .......... *B29C 64/393* (2017.08); *B29C 64/209* (2017.08); *B33Y 10/00* (2014.12); *B33Y 50/02* (2014.12); *G06K 9/6269* (2013.01); *G06K 9/6297* (2013.01); *G06N 3/04* (2013.01)

(58) Field of Classification Search
None
See application file for complete search history.

(56) References Cited

U.S. PATENT DOCUMENTS

| | | | |
|---|---|---|---|
| 7,853,351 | B2 | 12/2010 | Corey |
| 9,280,308 | B2 | 3/2016 | Kobayashi |
| 9,724,876 | B2 | 8/2017 | Cheverton et al. |
| 9,747,394 | B2 | 8/2017 | Nelaturi et al. |

(Continued)

FOREIGN PATENT DOCUMENTS

| | | |
|---|---|---|
| CN | 101943896 | 1/2011 |
| CN | 106802626 | 6/2017 |

OTHER PUBLICATIONS

Aminzadeh, Masoumeh, "A machine vision system for in-situ quality inspection in metal powder-bed additive manufacturing", Dec. 2016.*

(Continued)

*Primary Examiner* — Carlos R Ortiz Rodriguez
(74) *Attorney, Agent, or Firm* — Byrne Poh LLP

(57) ABSTRACT

Additive manufacturing systems using artificial intelligence can identify an anomaly in a printed layer of an object from a generated topographical image of the printed layer. The additive manufacturing systems can also use artificial intelligence to determine a correlation between the identified anomaly and one or more print parameters, and adaptively adjust one or more print parameters. The additive manufacturing systems can also use artificial intelligence to optimize one or more printing parameters to achieve desired mechanical, optical and/or electrical properties.

21 Claims, 8 Drawing Sheets

(56) References Cited

U.S. PATENT DOCUMENTS

| | | |
|---|---|---|
| 9,767,226 B2 | 9/2017 | Chen et al. |
| 9,855,698 B2 | 1/2018 | Perez et al. |
| 2008/0056582 A1 | 3/2008 | Matusik et al. |
| 2008/0091295 A1 | 4/2008 | Corey |
| 2014/0324204 A1 | 10/2014 | Vidimce et al. |
| 2015/0009301 A1 | 1/2015 | Ribnick et al. |
| 2015/0045928 A1 | 2/2015 | Perez et al. |
| 2015/0066440 A1 | 3/2015 | Chen et al. |
| 2016/0023403 A1 | 1/2016 | Ramos et al. |
| 2016/0167306 A1 | 6/2016 | Vidimce et al. |
| 2016/0236416 A1 | 8/2016 | Bheda et al. |
| 2017/0056966 A1 | 3/2017 | Myerberg et al. |
| 2017/0056967 A1 | 3/2017 | Fulop et al. |
| 2017/0056970 A1 | 3/2017 | Chin et al. |
| 2017/0232515 A1 | 8/2017 | DeMuth et al. |
| 2017/0252815 A1 | 9/2017 | Fontana et al. |
| 2017/0252816 A1 | 9/2017 | Shim et al. |
| 2017/0252820 A1 | 9/2017 | Myerberg et al. |
| 2017/0252821 A1 | 9/2017 | Sachs et al. |
| 2017/0252822 A1 | 9/2017 | Sachs et al. |
| 2017/0252823 A1 | 9/2017 | Sachs et al. |
| 2017/0252824 A1 | 9/2017 | Gibson et al. |
| 2017/0252825 A1 | 9/2017 | Fontana et al. |
| 2017/0252826 A1 | 9/2017 | Sachs et al. |
| 2017/0252827 A1 | 9/2017 | Sachs et al. |
| 2018/0036964 A1 | 2/2018 | DehghanNiri et al. |
| 2018/0056582 A1 | 3/2018 | Matusik et al. |
| 2018/0079125 A1 | 3/2018 | Perez et al. |
| 2018/0194066 A1 | 7/2018 | Ramos et al. |
| 2018/0236541 A1 | 8/2018 | Holenarasipura Raghu et al. |
| 2019/0001657 A1 | 1/2019 | Matusik et al. |

OTHER PUBLICATIONS

Adams et al., "Implicit Slicing Method for Additive Manufacturing Processes", in the Proceedings of the Solid Freeform Fabrication Symposium, Austin TX, Aug. 7-9, 2017, pp. 844-857.

Hodgson et al., "Slic3r Manual—Print Setting", Technical Paper, Mar. 17, 2018, pp. 1-10.

Lu et al., "A Layer-To-Layer Model and Feedback Control of Ink-Jet 3-D Printing", in IEEE Transactions on Mechatronics, vol. 20, No. 3, Jun. 2015, pp. 1056-1068.

Pertuz et al., "Analysis of Focus Measure Operators for Shape-From-Focus", in Intelligent Robotics and Computer Vision Group, Universitat Rovira i Virgili, Oct. 15, 2012, pp. 1-18.

Roschli et al., "ORNL Slicer 2: A Novel Approach for Additive Manufacturing Tool Path Planning", in the Proceedings of the Solid Freeform Fabrication Symposium, Austin TX, Aug. 7-9, 2017, pp. 896-902.

Shi et al., "Self-Calibrating Photometric Stereo", in Key Lab of Machine Perception, Peking University, Jun. 2010, pp. 1-8.

U.S. Appl. No. 10/252,466, filed Apr. 9, 2019, Ramos et al.

Brackett et al., "Topology Optimization for Additive Manufacturing", in the Proceedings of the Solid Freeform Fabrication Symposium, Aug. 8-10, 2011, Austin, TX, US, pp. 1-15.

Garanger et al., "Foundations of Intelligent Additive Manufacturing", Cornell University, Apr. 18, 2017, pp. 1-9.

Guo et al., "Additive Manufacturing Systems", in Intelligent Systems Automation and Control, Dec. 12, 2018, pp. 1-6, available online at: http://isaaclabrpi.com/project/additive-manufacturing-systems/.

International Search Report and Written Opinion dated Jun. 28, 2019 in International Patent Application No. PCT/US2019/024795.

Re:3D Inc., "Getting a Good Print", last updated Apr. 17, 2015, pp. 1-6, available at: http://wiki.re3d.org/index.php?title=Getting_a_good_print&oldid=6555.

Zheng et al., "Wide-Field, High Resolution Fourier Ptychographic Microscopy", Research Paper, California Institute of Technology, Jul. 2013, pp. 1-15.

\* cited by examiner

Print Quality

Layer Height

Shell Thickness

Retraction

Infill

Infill Density

Infill Pattern

Object Placement and Orientation

Location of the Object on the Build Plate

Orientation of the object on the build plate

Support

Support Type

Platform Adhesion Type

Speed and Temperature Settings

Print Head Speed

Build Plate Speed

Print Head Temperature

Build Plate Temperature

SYSTEMS, METHODS, AND MEDIA FOR ARTIFICIAL INTELLIGENCE FEEDBACK CONTROL IN ADDITIVE MANUFACTURING

TECHNICAL FIELD

The present disclosure relates to mechanisms for providing artificial intelligence feedback control in additive manufacturing.

BACKGROUND

Additive manufacturing systems, such as 3D printers and cell printers, are widely used to deposit multiple layers of natural, synthetic, or biological materials to manufacture objects through processes of extrusion, sintering, light polymerization, mechanosynthesis or electrohydrodynamic forces. The process of additive manufacturing fabricates an object through a layer deposition process, where the additive manufacturing printer keeps adding successive layers until the printed object is complete.

Generally, an object printed by an additive manufacturing printer is based on a production design. Three-dimensional modeling software (e.g., a CAD program) can be used to create a production design for an object to desired specifications. A slicing program can then translate the production design into numerical control code (e.g., G-code), which divides the design into a number of layers and which can then be used to instruct an additive manufacturing printer to print a physical representation of each individual layer of the production design. The goal of additive manufacturing is to print an object that adheres closely to the specifications of the production design.

A printed object can take anywhere from several hours to several days to complete, depending on the size and complexity of the production design. Current additive manufacturing systems are limited in the type of feedback they can provide and the corrective action that they can take after each layer of an object is printed. Often feedback is not provided until the entire object has printed. When feedback is provided during the printing process for an object, it is usually for the purpose of determining whether to stop or to continue printing the object.

In some additive manufacturing systems, feedback is provided by shadows created by the printed object when light is shined on the object. This method is limited, because the shadows obstruct areas of the printed object and prevent precise feedback. Precise feedback in additive manufacturing is useful to maintain quality and reproducible printed objects.

Accordingly, it is desirable to provide artificial intelligence feedback control (AIFC) for each printed layer of an object so that timely corrective action can be taken during the printing process for the object. It is also desirable to provide AIFC to achieve the desired mechanical, optical and/or electrical properties of a printed object, as well as to achieve a printed object that closely resembles its production design, or improves upon the production design.

SUMMARY

In accordance with some embodiments, systems, methods, and media for artificial intelligence feedback control in additive manufacturing are provided. More particularly, in some embodiments, additive manufacturing systems are provided, the systems comprising: a print head that is configured to print an object in a layer by layer manner; an illumination source for providing illumination to a surface of a printed layer of the object; an image sensor configured to capture an image of the printed layer; and at least one hardware processor configured to: receive a captured image; generate a three-dimensional topographical image of the printed layer; identify an anomaly in the printed layer from the generated topographical image using a first artificial intelligence algorithm; determine a correlation between the identified anomaly and one or more print parameters using a second artificial intelligence algorithm; and assign a value to one or more print parameters.

In some embodiments, methods for additive manufacturing are provided, the methods comprising: receiving a captured image produced by an image sensor configured to capture an image of a printed layer of an object printed in a layer by layer manner; generating a three-dimensional topographical image of the printed layer using a hardware processor; identifying an anomaly in the printed layer from the generated topographical image using a first artificial intelligence algorithm; determining a correlation between the identified anomaly and one or more print parameters using a second artificial intelligence algorithm; and assigning a value to one or more print parameters.

In some embodiments, non-transitory computer-readable media containing computer-executable instructions that, when executed by a processor, cause the processor to perform a method for additive manufacturing are provided, the method comprising: receiving a captured image produced by an image sensor configured to capture an image of a printed layer of an object printed in a layer by layer manner; generating a three-dimensional topographical image of the printed layer; identifying an anomaly in the printed layer from the generated topographical image using a first artificial intelligence algorithm; determining a correlation between the identified anomaly and one or more print parameters using a second artificial intelligence algorithm; and assigning a value to one or more print parameters.

BRIEF DESCRIPTION OF THE DRAWINGS

FIG. 3 is an example of an interface for an operator to input print parameters into a numerical control code generator in accordance with some embodiments.

DETAILED DESCRIPTION

In accordance with some embodiments of the disclosed subject matter, mechanisms (which can include systems, methods, devices, apparatuses, etc.) for additive manufacturing artificial intelligence feedback control (AIFC) are provided. AIFC can be useful, for example, to optimize the printing parameters of an additive manufacturing system to achieve desired mechanical, optical and/or electrical properties and/or desired accuracy of a printed object compared to a production design. AIFC can also be useful to identify anomalies in a printed layer and to take corrective action during a printing process.

As disclosed herein, in some embodiments, artificial intelligence can be used to learn from and improve upon additive manufacturing as described herein and to output feedback, information, data, and/or instruction ("AIFC"). The artificial intelligence algorithms can include one or more of the following, alone or in combination: machine learning, hidden Markov models; recurrent neural networks; convolutional neural networks; Bayesian symbolic methods; general adversarial networks; support vector machines; and/or any other suitable artificial intelligence algorithm. While AIFC is based on AI algorithms, AIFC can also use data collected during additive manufacturing that is not based on artificial intelligence algorithms.

Figure 1:
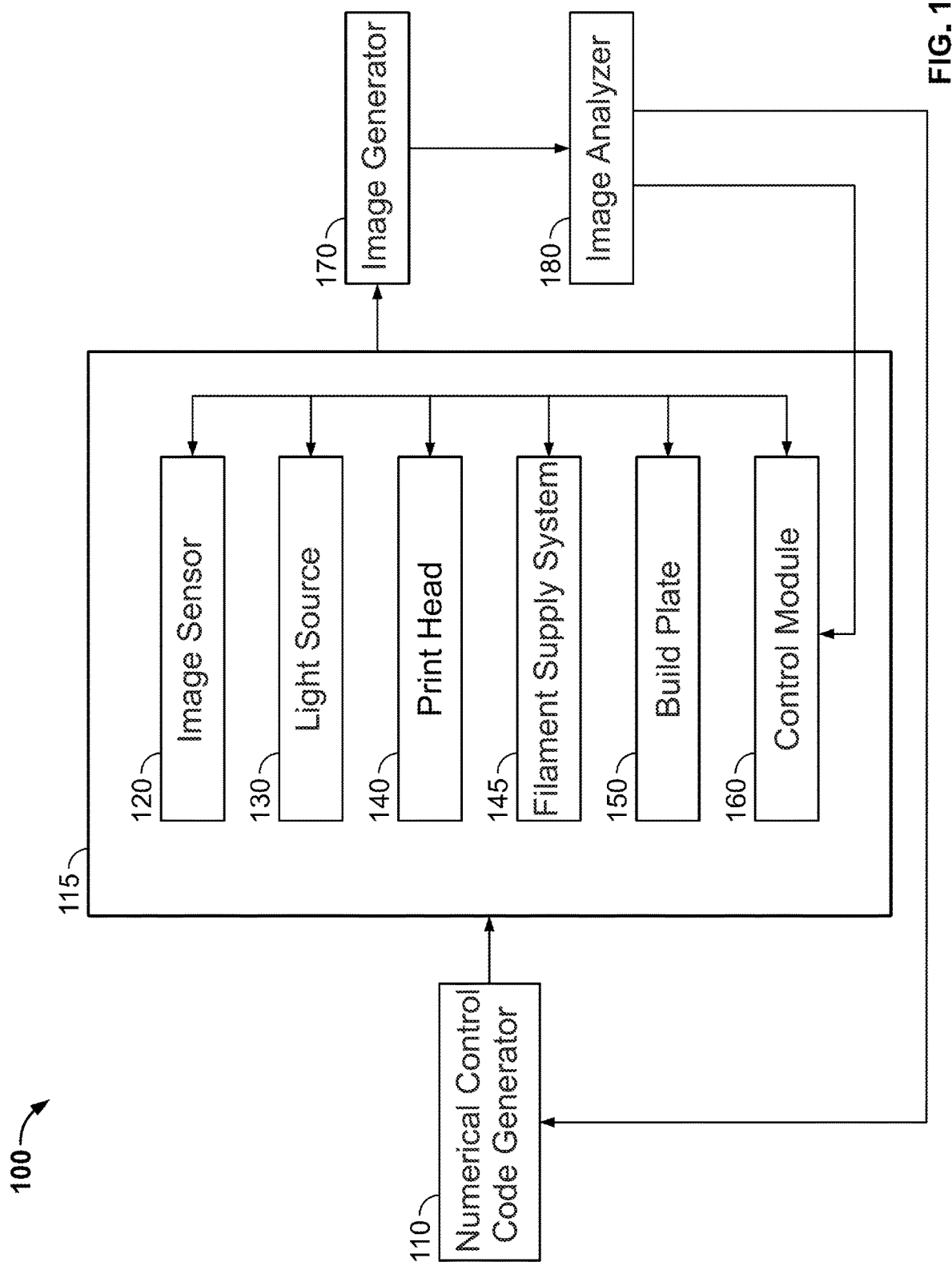
FIG. 1 is an example of an additive manufacturing system in accordance with some embodiments.

FIG. 1 illustrates an example additive manufacturing system 100 that can implement AIFC according to some embodiments of the disclosed subject matter. At a high level, the basic components of additive manufacture system 100, according to some embodiments, include numerical control code generator 110, additive manufacturing printer 115, image generator 170, and image analyzer 180. Additive manufacturing printer 115 can include image sensor 120, light source 130, print head 140, filament supply system 145, build plate 150 and control module 160. The functionality of the components for additive manufacturing system 100 can be combined into a single component or spread across several components. In some embodiments, the functionality of some of the components (e.g., numerical control code generator 110, image generator 170, and/or image analyzer 180) can be performed remotely from the additive manufacturing printer 115.

Note that additive manufacturing system 100 can include other suitable components not shown. Additionally or alternatively, some of the components included in additive manufacturing system 100 can be omitted.

Although the following description refers to using AIFC with a fused deposition modeling additive manufacturing printer, in some embodiments, the AIFC described herein can be used with any suitable 3-D printing technology, including stereolithography (SLA), electron beam melting, direct metal deposition (electrohydrodynamic printing) and selective laser sintering.

In some embodiments, additive manufacturing printer 115 can include one or more image sensors 120 for capturing images and/or video during the printing process. The image sensor(s) 120 can be configured to capture images (or video) of an object while and/or after each layer of the object is printed. Image sensor 120 can be, for example, a charge coupled device (CCD) or a complementary metal oxide semiconductor (CMOS) sensor like what might be used in a digital still and/or video camera. Image sensor 120 can also include an infrared (IR) camera for capturing thermal images and/or video of an object and performing temperature calculations. Image sensors 120 can be located at different positions and angles relative to build plate 150 and/or print head 140.

In some embodiments, additive manufacturing printer 115 can include a single light source 130 or multiple light sources (e.g., a multi-light vector), located at different positions and angles relative to build plate 150 and/or relative to image sensor 120 (e.g., the light source can be located circumferentially around image sensor 120). The illumination can vary by size, number of light sources used, and/or the position and angle of illumination. The illumination can be used to illuminate a printed layer of an object so that image sensor 120 can capture images and/or video of the object.

The captured images and/or video can be stored in memory and can be used to create three-dimensional topography images, and/or other suitable images, of the printed layer, as discussed herein in connection with image generator 170.

Figure 2:
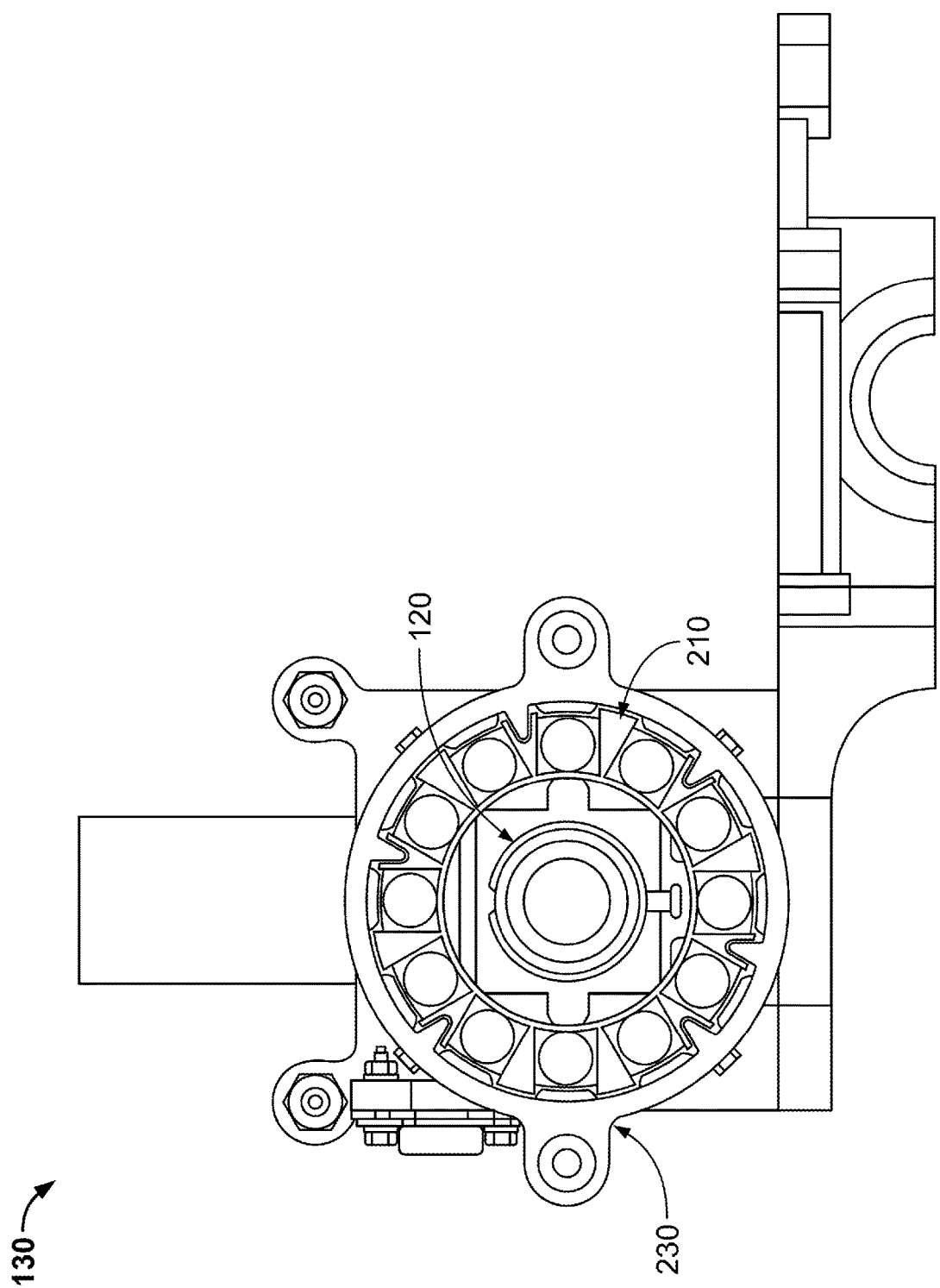
FIG. 2 is an example of a camera and a light source that can be used with an additive manufacturing printer in accordance with some embodiments.

FIG. 2 shows an example of camera 120 and light source 130 that can be used with additive manufacturing printer 115. FIG. 2 includes a camera 120 surrounded by a light-emitting diode (LED) ring 210 resting in LED holder 230. In some embodiments, control module 160 controls the individual LEDs within LED ring 210, determining which LEDs should be illuminated. The control of the individual LEDs within LED ring 210 can be determined by the requirements of the topographical imaging technique used to generate images of the printed layer.

As described above, additive manufacturing printer 115 can also include one or more print heads 140 and one or more build plates 150. Print head(s) 140 and/or build plate(s) 150 can move with respect to the other in X (width), Y (length) and Z (height) dimensions. Print head(s) 140 can hold filament, supplied by filament supply system 145, that is extruded in a layer by layer manner through one or more nozzles of print head(s) 140. In some embodiments, the temperature of the print head nozzle(s) can be controlled to heat up the filament stored in print head(s) 140 to keep the filament in a flowable form that can be deposited (e.g., when print head(s) 140 and/or build plate(s) 150 move with respect to the other, and/or when print head(s) 140 and/or build plate(s) 150 are static). The extruded material can fuse to build plate(s) 150 (as is the case for the first extruded layer) or to a previously deposited extruded layer. Other aspects of print head(s) 140 and/or build plate(s) 150 that can be controlled include, for example, paths that print head(s) 140 and/or build plate(s) 150 follow during movement, amount(s) that the print head(s) and/or build plate(s) 150 move with respect to the other along the Z-axis dimension when transitioning between layers of a production design, orientation(s) of print head(s) 140 and/or build plate(s) 150 with respect to the other, speed(s) of movement of print head(s) 140 and/or build plate(s) 150, and amount(s) and rate(s) of filament that print head(s) 140 deposit. In some embodiments, the print path can be defined by at least two sets of X-Y-Z coordinates. During operation, the print head(s) and/or build plate(s) can be controlled to move with respect to the other and the print head(s) can release filament in a desired infill pattern. In some embodiments, print head(s) 140 and/or build plate(s) 150 can be controlled by code from numerical control code generator 110 and/or control module 160.

In some embodiments, build plate 150 can be heated to a predetermined temperature and can be oriented in different directions.

In some embodiments, control module 160, which, in some embodiments, can include a controller and controller interface, can control any suitable one or more settings (e.g., temperature, speed, orientation, etc.) of the components (e.g., numerical control code generator 110, image sensor 120, light source 130, print head 140, build plate 150, image generator 170, and image analyzer 180) of additive manufacturing system 100, as well as communications, operations (e.g., capturing images of the printed object, enabling light source 130, etc.), and calculations performed by, and between, components of the additive manufacturing system. Control system 108 can include any suitable hardware (which can execute software in some embodiments), such as, for example, computers, microprocessors, microcontrollers, application specific integrated circuits (ASICs), field-programmable gate arrays (FGPAs), and digital signal processors (DSPs) (any of which can be referred to as a hardware processor), encoders, circuitry to read encoders, memory devices (including one or more EPROMS, one or more EEPROMs, dynamic random access memory ("DRAM"), static random access memory ("SRAM"), and/or flash memory), and/or any other suitable hardware elements. In some embodiments, individual components within additive manufacturing system 100 can include their own software, firmware, and/or hardware to control the individual components and communicate with other components in additive manufacturing system 100.

In some embodiments, communication between control module 160 and other components of additive manufacturing system 100, and/or communication between control module 160 and other components within additive manufacturing printer 115, can use any suitable communication technologies, such as analog technologies (e.g., relay logic), digital technologies (e.g., RS232, ethernet, or wireless), network technologies (e.g., local area network (LAN), a wide area network (WAN), the Internet), Bluetooth technologies, Near-field communication technologies, Secure RF technologies, and/or any other suitable communication technologies.

In some embodiments, operator inputs can be communicated to control module 160 using any suitable input device (e.g., a keyboard, mouse or joystick).

In addition to the components shown in FIG. 1, additive manufacturing printer 115 can also include other components, for example, a temperature sensor, a humidity sensor, an accelerometer for measuring acceleration and any unintended motion of print head 140 (such as a jolt, shudder etc.), and a display monitor for displaying images. Additive manufacturing printer 115 can also include one or more actuators for orienting and/or moving image sensor 120, illumination source 130, print head 140, and/or build plate 150.

FIG. 1 also shows numerical control code generator 110. In some embodiments, numerical control code generator 110 can be configured to receive a three-dimensional design (e.g., a Computer Aided Design (CAD) model) (referred to herein as a "production design") of an object to be printed. The production design can be received in any suitable format (e.g., standard tessellation language (.stl), drawing standard (DWS), or drawing (DWG) file formats) that can be processed by numerical control code generator 110.

Numerical control code generator 110 can be configured to translate a production design into instructions for additive manufacturing printer 115 to print a physical representation of the production design. In some embodiments, numerical control code generator 110 can include an interface for an operator to enter certain print parameters as described in connection with FIG. 3. Print parameters can also include, but are not limited to, one or more of: print features of additive manufacturing machine 115 (e.g., print head size, type of filament extruded, 3D printing technique, etc.); print path; filament feed rate; and specifications of a production design (e.g., what a printed design should look like, desired mechanical, optical and/or electrical properties of the design, etc.).

Based on one or more print parameters, numerical control code generator 110 can apply a slicing algorithm to intersect a production design with parallel planes that are spaced apart at a predetermined distance in a Z direction to create two-dimensional or three-dimensional layers. For example, if an object to be printed is 5 mm in the Z direction and the desired layer thickness is 0.2 mm in the Z direction, then the production design of the object can be sliced into 25 layers that are 0.2 mm thick in the Z direction. In addition to slicing a production design, numerical control code generator 110 can be further configured to generate numerical control code for each layer to be printed based on one or more: print parameters; AIFC from one or more prior printed layers of a printed object that is currently printing; AIFC from other printed objects (some of which may be incorporated into the production design); and print features of additive manufacturing printer 115.

In other embodiments, the slicing algorithm can be configured to determine a first layer only and to generate numerical control code for that first layer. The numerical control code for each subsequent layer of a printed object can be generated based on one or more of: AIFC from one or more prior printed layers of a printed object that is currently printing; AIFC from other printed objects (some of which may be incorporated into the production design); desired mechanical, optical and/or electrical properties and specifications for the production design of the printed object; and input parameters entered by an operator and/or print features of the additive manufacturing printer 115. In some embodiments, the slicing algorithm can be omitted altogether and the numerical control code can be generated based on one or more of: AIFC from other printed objects (some of which may be incorporated into the production design); desired mechanical, optical and/or electrical properties and specifications for the production design of the printed object; input parameters entered by an operator; and/or print features of the additive manufacturing printer 115. In some embodiments, the numerical control code generator can also consider non-controllable variables (i.e., variables that are non-controllable without human intervention), for example, including, but not limited to, ambient humidity, temperature and light exposure, voltage variation, wear and tear of additive manufacturing printer 115, and the total filament supply available to print head 140.

FIG. 3 illustrates an example interface 300 for an operator to input print parameters into numerical control code generator 110 according to some embodiments of the disclosed subject matter.

Note that interface 300 can include fields to control other suitable print parameters that are not shown. Additionally or alternatively, some of the print parameters included in interface 300 can be omitted in some embodiments. Further, any and all print parameters included in interface 300 can alternatively be generated automatically by the numerical control code generator and not be inputted by an operator. In some embodiments, an operator can input print parameters for the first layer of a production design, and numerical control code generator 110 can use artificial intelligence algorithms and other methods disclosed herein to generate print parameters for subsequent layers of the printed design.

As shown, interface 300 can include fields to control print quality parameters like layer height, shell thickness, and retraction.

Layer height refers to the height of a layer of a printed object. The height of a layer can affect printing resolution. For example, a short layer can create a more detailed print and a smoother surface than a taller layer. However, an object with shorter layers can take longer to print. Conversely, a taller layer can correspond to a lower resolution print and a rougher surface. An object comprising tall layers may be printed more quickly than the same object with shorter layers. Any suitable layer height can be used in some embodiments.

Shell thickness refers to the thickness of the outer walls of a printed object. Any suitable shell thickness can be used in some embodiments.

Retraction refers to ensuring that no filament is extruded from a print head when the print head moves over an area where there is no print specified. In some embodiments, retraction can be enabled or disabled.

Interface 300 can also include fields to control print speed settings for controlling print head speed and/or build plate speed. Print speed refers to how fast a print head and/or a build plate moves when the print head prints. Any suitable print speed can be used in some embodiments. Based on the print speed, the amount of material that needs to be extruded (i.e., the feed rate) can be calculated. Any suitable feed rate can be used in some embodiments.

Interface 300 can also include fields to control temperature settings for controlling print head temperature and/or build plate temperature. It may be necessary to change the temperature of the print head when the print speed changes in order to ensure that the extruded filament is sufficiently heated for deposition. Any suitable print head temperature can be used in some embodiments.

Interface 300 can also include fields to control infill density and infill pattern settings.

Infill density refers to the structure that is printed inside an object and can be specified, for example, by percentage. Any suitable infill density can be used in some embodiments. 100% infill density refers to a solid infill density without intended gaps.

Infill pattern refers to the pattern of the infill. Any suitable infill pattern(s) can be used in some embodiments. For example, in some embodiments, infill patterns can include honeycomb, triangular, grid, and rectangular. Infill density and infill pattern can influence print weight, printed object strength, total print time, and external properties. Infill pattern can also influence mechanical, optical and/or electrical properties. The infill density and infill pattern can be set for a particular layer or for an entire object in some embodiments.

Further, interface 300 can include fields to control support settings including support type and platform adhesion type.

Some printed objects may have overhanging parts and therefore may need support to prevent the extruded filament from falling down during the printing process. The support settings can be used to specify where the support can be placed. Any suitable support settings can be use in some embodiments.

Platform adhesion settings can be used to improve adhesion of a printed layer to build plate 150. Different types of platform adhesion settings that can be specified include: a raft setting which adds extra filament in the form of a thick grid between the base layer of a printed object and a build plate; a brim setting that adds extra lines of filament around a first layer of a printed object; and a skirt setting that adds a line of filament around an object on a first printed layer. Using certain platform adhesion settings can help decrease the amount of warping in a printed object. Any suitable platform adhesion settings can be used in some embodiments.

Interface 300 can also include fields settings related to object placement and orientation. These settings include the location of the printed object on build plate 150, as well as the orientation of the printed object on build plate 150. Any suitable object placement and/or orientation settings can be used in some embodiments.

In some embodiments, generated numerical control code can describe a print path for the relative movement of print head 140 and/or build plate 150. The print path can be defined by two sets of coordinates in X-Y-Z dimensions (setpoints), as well as instructions specifying a manner of moving between the setpoints. The generated numerical control code can specify a speed of movement of print head 140 and/build plate 150 with respect to the other while moving between a pair of consecutive points along the print path, a temperature of the filament (or the temperature of the print head nozzle) between a pair of consecutive points, and/or a feed rate of the filament between a pair of consecutive points. Generated numerical control code can specify where print head 140 should extrude filament, and/or where it should refrain from releasing filament. All the parameters included in the generated numerical control code are also considered "print parameters."

One or more of the print parameters described above, as well as non-controllable variables, can affect properties of a printed object, such as layer anomalies, surface roughness, print resolution, total build time, amount of extruded material used for the printed object, and the mechanical, optical and/or electrical properties of the printed object. Mechanical properties can include maximum tensile strength ($R_m$), yield strength ($Rp_{2\%}$), elongation at break ($A_\%$), Young's modulus (E), fatigue ($\sigma_d$), Poisson's ratio, mass, and specific gravity. Optical properties can include absorption, reflection, transmission, and refraction. Electrical properties can include electrical resistivity and conductivity. The disclosed mechanical, optical, and electrical properties are just examples and are not intended to be limiting.

AIFC can be used to optimize for desired mechanical properties, optical properties, electrical properties, and/or any suitable characteristics of an object being printed. AIFC can also be used to take corrective action when printing an object. The corrective action can include changing print parameters of a next layer or targeted future layers of an object that is currently in print. In some embodiments, AIFC can be used to improve upon a production design.

As show in FIG. 1, additive manufacturing system 100 can include image generator 170 that can process captured images and/or video of the printed layers of an object. In some embodiments, image generator 170 can include hardware or software configured for storing captured images and/or video and for generating a three-dimensional topography images of the printed layer(s), and/or other suitable images, from the captured images and/or video.

Different topographical imaging techniques can be used (including but not limited to, shape-from-focus algorithms, shape-from-shading algorithms, photometric stereo algorithms, and Fourier ptychography modulation algorithms) with a predefined size, number, and position of illuminating light to generate one or more three-dimensional topography images of each printed layer. The generated topographical images can provide volumetric information related to completed layers of a printed object and/or partially printed object, overall dimensions of each layer of a printed object and/or partially printed object, features of each layer of a printed object and/or partially printed object, and information regarding anomalies (such as amount, distribution, anomaly type, etc.) found on one or more layers of a printed object and/or partially printed object.

An example of a shape-from-focus algorithm that can be adapted for use by image generator 170 in additive manufacturing system 100 is described by Said Pertuz et al., "Analysis of Focus Measure Operators for Shape-from-Focus," Pattern Recognition, vol. 45, issue 5, pp. 1415-1432, which is hereby incorporated by reference herein in its entirety. The disclosed method is just an example and is not intended to be limiting.

An example of a shape-from-shading algorithm that can be adapted for use by image generator 170 in additive manufacturing system 100 is described by Byungil Kim et al., "Depth and Shape from Shading using the Photometric Stereo method," CVGIP: Image Understanding, vol. 54, no. 3, pp 416-427, 1991, which is hereby incorporated by reference herein in its entirety. The disclosed method is just an example and is not intended to be limiting.

An example of a photometric stereo algorithm that can be adapted for use by image generator 170 in additive manufacturing system 100 is described by Jose R. A. Torreao, "Estimating 3-D Shape from the Optical Flow of Photometric Stereo Images," Proceedings of the 6th Ibero-American Conference on AI: Progress in Artificial Intelligence (IBERAMIA 1998), Helder Coelho (Ed.), Springer-Verlag, London, UK, UK, 253-261, which is hereby incorporated by reference herein in its entirety. The disclosed method is just an example and is not intended to be limiting.

An example of a Fourier ptychography modulation algorithm that can be adapted for use by image generator 170 in additive manufacturing system 100 is described by Guoan Zeng et al. "Wide-field High-resolution Fourier Ptychographic Microscopy," Nature Photonics, vol. 7, pp. 739-745, 2013, which is hereby incorporated by reference herein in its entirety. The disclosed method is just an example and is not intended to be limiting.

Figure 4:
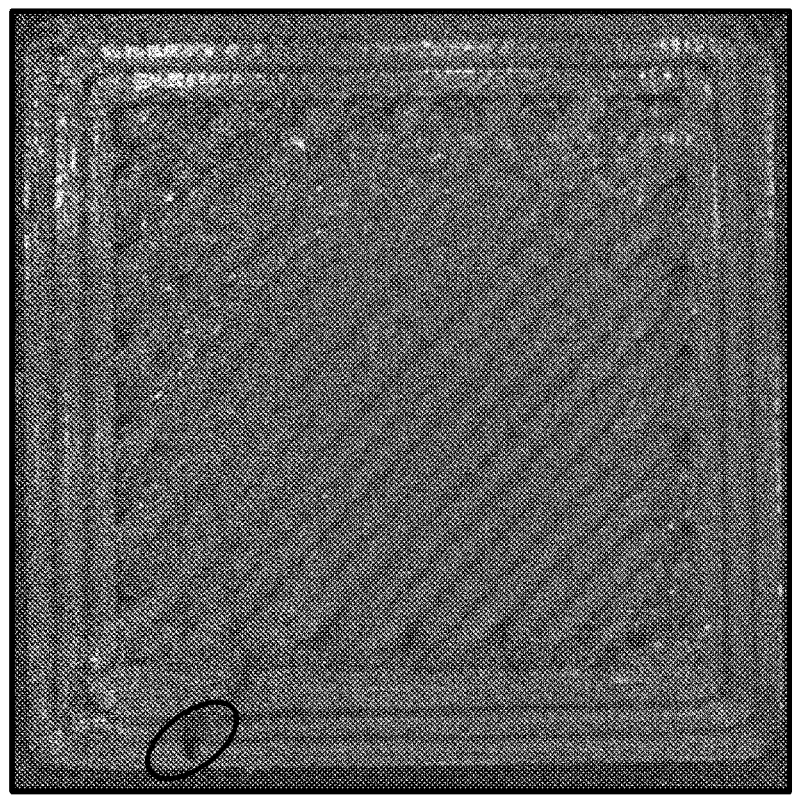
FIG. 4 is an example of an image of a printed layer showing an unintended gap in the deposited filament that can be captured in accordance with some embodiments.
Figure 5C:
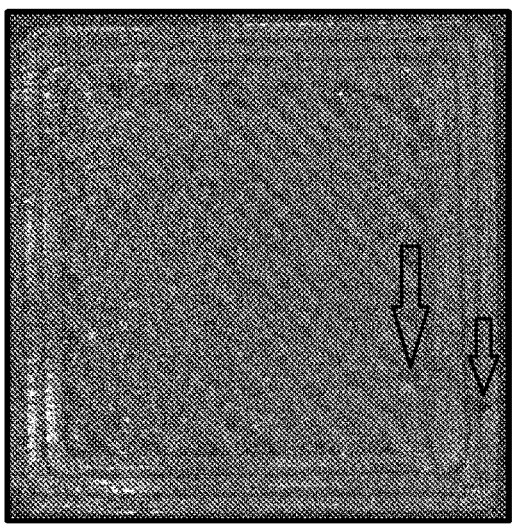
FIGS. 5A, 5B, and 5C are examples of images of various printed layers showing unintended thread-like artifacts and other disruptions in a printed layer that can be captured in accordance with some embodiments.
Figure 5B:
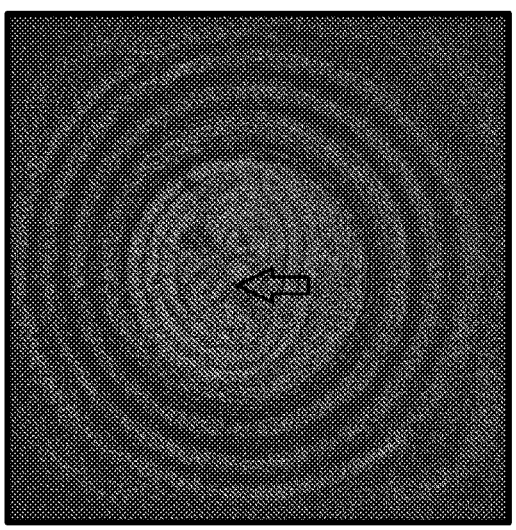
Figure 5A:
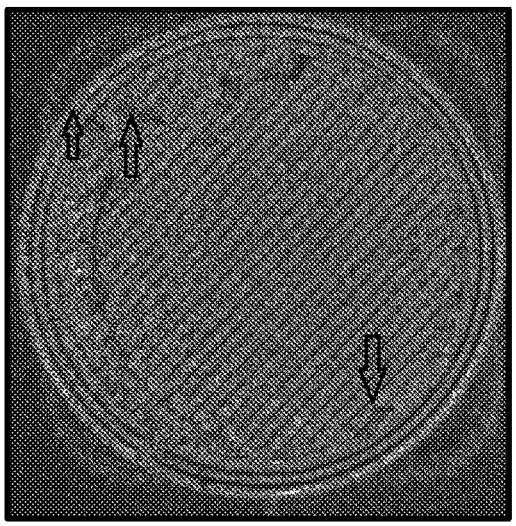

In some embodiments, topographical images and/or other suitable images generated by image generator 170 can provide information such as anomaly rate and distribution, anomaly type, deposited filament at various points along a print path, etc. For example, as shown in FIG. 4, captured image 400 of a printed layer shows an unintended gap in the deposited filament. In another set of examples, as shown in FIGS. 5A, 5B, and 5C, the captured images of various printed layers show unintended thread-like artifacts and other disruptions in the printed layer.

In some embodiments, image analyzer 180 can be configured to receive generated topographical images and/or other suitable images from image generator 170 and visually recognize and identify one or more anomalies on a printed layer. In some embodiments this can be done by comparing the following to identify differences: actual features of a printed layer as obtained from a two-dimensional or three-dimensional topographical image, a detected print path map of the printed layer, and/or an image of the layer; and features of the printed layer, as specified in generated numerical code and/or a production design for the layer. In some embodiments, one or more artificial intelligence algorithms can be used to identify anomalies based on the differences. These anomalies can include, for example differences between an actual printed layer and production design and/or generated numerical code for the printed layer with respect to: the perimeter dimensions of the layer; the dimensions of deposited filament between setpoints; infill density; infill pattern; surface roughness; the print path; and/or any other variation. The identification of the anomaly can include classifying the anomaly, as well as identifying its size, shape, X-Y-Z location, and/or any other suitable characteristic. In some embodiments, any suitable artificial intelligence algorithm(s) can be used. For example, in some embodiments, the artificial intelligence algorithms can include one or more of the following, alone or in combination: machine learning; hidden Markov models; recurrent neural networks; convolutional neural networks; Bayesian symbolic methods; general adversarial networks; support vector machines; and/or any other suitable artificial intelligence algorithm.

In some embodiments, algorithms that are not based on artificial intelligence can be used to identify anomalies.

In some embodiments, image analyzer 180 can be preprogrammed to recognize certain anomalies (e.g., unintended gaps or curled edges, warped or uneven patterns, points of excessive extrusion, thread-like or other foreign artifacts and/or any other disruption in the printed layer) in a received image of a printed layer. Based on the preprogrammed anomalies, image analyzer 180 can process a generated image for a completed print layer to determine whether the processed image includes any anomalies similar to the preprogrammed anomalies and identify one or more locations for any such anomaly on a printed layer.

In some embodiments, image analyzer 180 can be further configured to determine and record a correlation between a detected anomaly and one or more print parameters. For example, by using a suitable artificial intelligence algorithm, the image analyzer can determine one or more print parameters that may correlate with a detected anomaly. For example, image analyzer 180 may discover the following example correlations: disruptions occur when a print head is at certain temperatures and not at others; certain print speeds, and not others, cause a high number of unintended gaps; and certain infill patterns, at certain locations in an object, cause a certain type of anomaly.

In some embodiments, in response to detecting a correlation between a detected anomaly and one or more print patterns, image analyzer 180 can provide information, data, and/or instructions which alter the manner in which one or more layers of an object being printed or one or more objects to be printed in the future are printed. For example, in some embodiments, the image analyzer can communicate the discovered correlations and/or instructions for adaptively adjusting print parameter settings to numerical control code generator 110, control module 160 and/or to any other device. The numerical control code generator 110 and/or control module 160 can then use the information to make adjustments to the print parameters in the numerical control code for any subsequent layers of an object that is currently being printed. In some embodiments, print parameters can be adjusted so that a next layer or any future layer compensates for anomalies found in a prior layer. For example, if an unintended gap is detected in a print layer, the numerical control code for the next layer can include instructions to fill the gap when depositing the filament located above the gap. In another example, when an unintended gap is found in a lower portion of an object, the numerical control code for a symmetrical layer in the upper portion of an object can include instructions to compensate for the gap.

In some embodiments, image analyzer 180 can be configured to measure mechanical, optical and/or electrical of a completed printed object.

In some embodiments, image analyzer 180 can be configured to detect a correlation between one or more print parameters and fewer anomalies in a printed layer and/or a completed printed object. In further embodiments, image analyzer 180 can be configured to detect a correlation between one or more print parameters and the measured mechanical, optical and/or electrical properties of a completed printed object. In response to detecting one or more such correlations, image analyze can provide information, data, and/or instructions which alter the manner in which one or more layers of an object being printed or one or more objects to be printed in the future are printed. In some embodiments, image analyzer 180 can provide information, data, and/or instructions, for example to a three-dimensional modeling software, to improve upon a production design.

In some embodiments, image analyzer 180 can use generated topographical images, and/or other generated images, for a printed layer, as well as generated numerical control code for the printed layer, to learn a relationship between non-controllable variables (i.e., variable that are non-controllable without human intervention) and the resulting print head motion, as well as the anomalies (e.g., unintended gaps or curled edges, warped or uneven patterns, points of excessive extrusion, deviations from the print path specified in the numerical control code, unintended thread-like or other foreign artifacts and/or any other disruption in the printed layer) in a deposited layer. In response to detecting a correlation between non-controllable variables and the resulting print head motion, as well as anomalies, image analyzer 180 can provide information, data, and/or instructions which alter the manner in which one or more layers of an object being printed or one or more objects to be printed in the future are printed.

In some embodiments, information on the correlations can be used to train one of more AI mechanisms as described herein.

In some embodiments, after a layer is printed, image analyzer 180 can be configured to compare the completed printed layer with one or more prior layers to detect and record anomalies, to compare and record anomaly rates and patterns, and to provide instructions to numerical control code generator 110 and/or control module 160 to adjust the print parameters to optimize an overall design of the object (e.g., to obtain the desired mechanical, optical and/or electrical properties or to achieve a printed design that closely resembles the production design) or to optimize the operation of the print job (e.g., speed-up deposition rate, or minimize the amount of material needed). The comparison between a completed layer and previous layers to identify anomalies can also be used to better assign causality to the print parameters of the additive manufacturing system 100 and to make appropriate adjustments for the next or any subsequent layers of a partially printed object, as well as to optimize future print jobs of a similar or different object.

In some embodiments, image analyzer 180 can be configured to analyze the overall anomaly rate for the current and/or prior layers of a partially printed object, and based on AIFC from similar print jobs, provide instructions to the numerical control code generator 110 and/or control module 160 to adjust the print parameters for the next and/or any future layers of the partially printed object to obtain the desired mechanical, optical and/or electrical properties.

In some embodiments, after a layer is printed, an algorithm, not based on artificial intelligence, can be used to identify anomalies that are related to the particular calibration of the specific additive manufacturing printer being used. Appropriate adjustments can be made to the numerical control code for subsequent layers and future print jobs to account for the calibration of the specific additive manufacturing printer.

In some embodiments, if the anomalies in a printed layer or layers exceed certain predetermined tolerances, then the print job for the printed object can be stopped prior to completion. Data collected for the failed print job can provide information, data, and/or instructions to numerical control code generator 110, control module 160 and/or any computer system collecting training data related to print processing performed by additive manufacturing printer 115.

In some embodiments, image analyzer 180 can be further configured to send anomaly data (e.g., the distribution, pattern and rate of anomalies) for a printed object, as well as automatically recommended print adjustments to a three-dimensional modeling software to eliminate or modify structures in the design corresponding to the anomalies.

Figure 6:
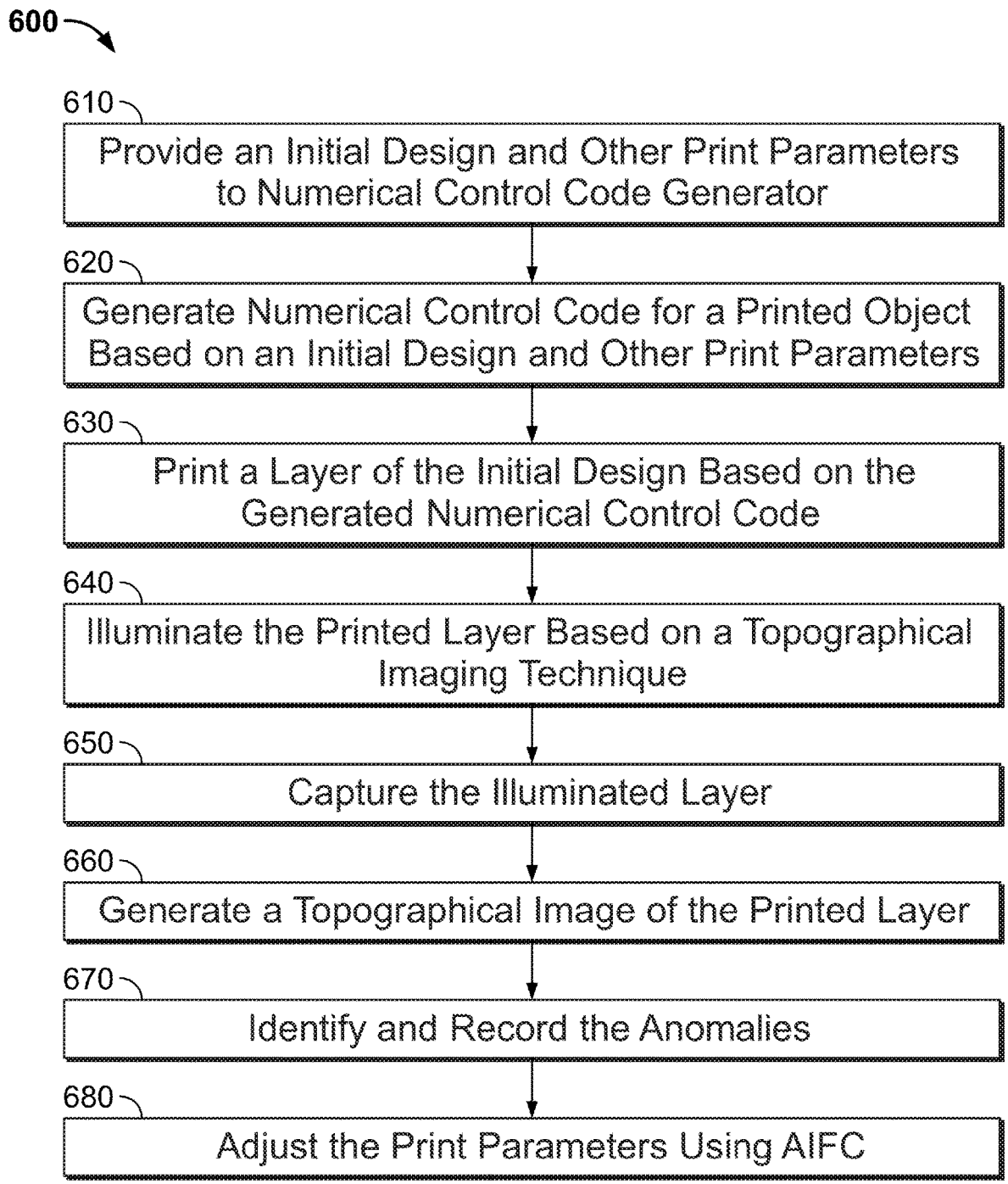
FIG. 6 is an example of an additive manufacturing printing operation (at a high level) in accordance with some embodiments.

FIG. 6, with further reference to FIGS. 1-3, shows at a high level, an example of an additive manufacturing printing operation using AIFC, in accordance with some embodiments of the disclosed subject matter. In some embodiments, additive manufacturing process 600 can use additive manufacturing system 100.

At 610, a production design specifying what a printed object should look like, as well as desired mechanical, optical and/or electrical properties for the printed object are provided to numerical control code generator 110. In some embodiments, some initial print parameters are entered by an operator. In some embodiments, a production design is provided to numerical control code generator 110, and image analyzer 180, using AIFC, determines desired mechanical, optical and/or electrical properties for the production design.

In some embodiments, an operator can input a set of rules for image analyzer 180 to resolve conflicting goals during the additive manufacturing printing process. For example, a user can specify that achieving optimal mechanical properties of a printed object should be prioritized over: print speed; integrity to the production design; and reducing the amount of filament used. An operator can also specify what mechanical, optical and/or electrical properties are most important for a printed object, so that image analyzer 180 can provide instructions for adjusting print parameters that optimize for those mechanical, optical and/or electrical properties.

Figure 7A:
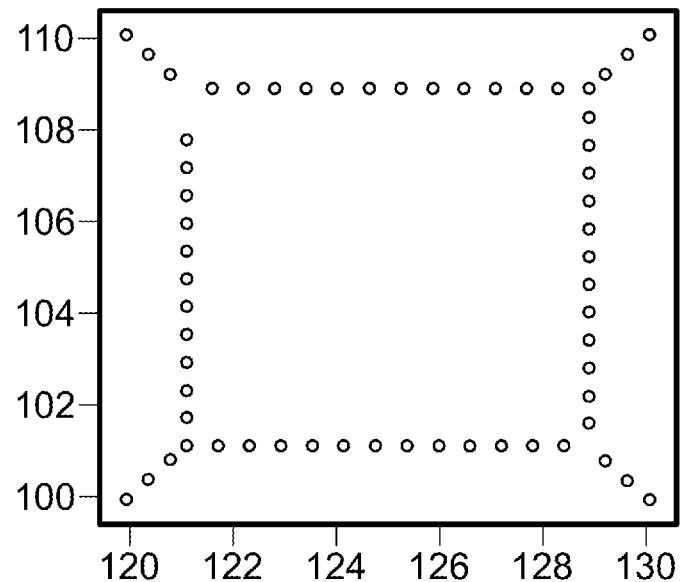
FIG. 7A is an example of a simulation of a set of setpoints for a printed layer that might be included in numerical control code in accordance with some embodiments.
Figure 7B:
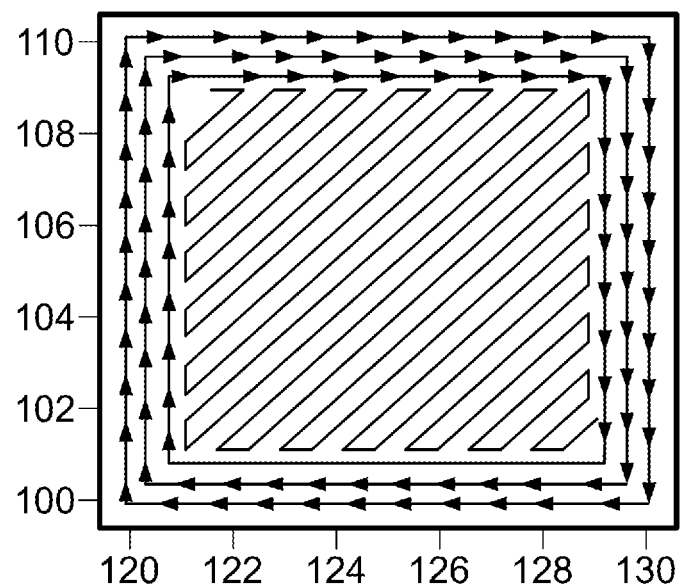
FIG. 7B is an example of a simulation of what a traversed print path might look like in accordance with some embodiments.

At 620, numerical control code generator 110 can generate numerical control code for a layer of a printed object based on one or more of: input parameters entered by an operator, the print features of additive manufacturing printer 115; the specifications of the production design (including mechanical, optical and/or electrical properties); AIFC from one or more prior printed layers of the partially printed object and/or AIFC from other printed objects. The generated numerical control code can include a set of setpoints (e.g., a plurality of X-Y-Z coordinates) for print head 140 and/or build plate 150 to traverse. FIG. 7A shows an example simulation of a set of setpoints for a printed layer that might be included in the numerical control code. The generated numerical control code can also include instructions defining how the print head and/or build plate should traverse the individual setpoints. An example simulation of what a traversed print path might look like, based on the included instructions, is shown, for example, in FIG. 7B.

In some embodiments, the generated numerical control code can also specify certain print parameters, including but not limited to, a speed of print head 140 and/or build plate 150 between setpoints, a temperature of the nozzle of print head 140 and/or build plate 150 between setpoints, an amount of filament deposited between setpoints, an infill density between setpoints, and an infill pattern between setpoints.

At 630, print head 140 can deposit filament for a layer of a production design according to instructions provided by numerical control code generator 110 and/or control module 160.

At 640, light source 130 can illuminate the printed layer based on a specified topographical imaging technique and/or other imaging technique (as described above).

At 650, image sensor 120 can capture an image of the illuminated printed layer.

At 660, image generator 170 can generate one or more topographical images, and/or any other suitable image(s), of the printed layer based on the images captured by image sensor 120. In some embodiments, the generated image(s) of the printed layer can comprise a series of captured images that are tiled or stitched together.

In further embodiments, the actual print path for the printed layer can be determined from the one or more topographical images, and/or other suitable images generated by image generator 170.

At 670, image analyzer 180 can use the generated topographical images, and/or other generated images, for the printed layer, as well as the generated numerical control code for the printed layer, to determine and record the anomalies (e.g., unintended gaps or curled edges, warped or uneven patterns, points of excessive extrusion, deviations from the print path specified in the numerical control code, unintended thread-like or other foreign artifacts and/or any other disruption in the printed layer) in the extruded layer.

In some embodiments, image analyzer 180 can extract and plot a print path for the printed layer from the setpoints and instructions contained in the generated numerical control code. The image analyzer can convert the plotted print path to pixels, and overlay the pixels on a print path obtained from the generated images for the printed layer, and determine difference between the pixels and the print path. In some embodiments, image analyzer 180 can convert the print path obtained from the generated images for the printed layer into print points in a coordinate system and compare these print points to print points along the plotted path extracted from the generated numerical control code.

If the print path for the printed layer as obtained from the generated images is the same as the extracted print path from the generated numerical control code, the difference between them will be zero or close to zero. A number greater than zero describes the amount of error detected between the actual print path and the print path specified in the generated numerical control code. A comparison of the print paths can also indicate where errors occurred along the print path.

At 680, image analyzer 180 can analyze the number of anomalies and the pattern of the anomalies (including the deviations between the actual path and the print path in the generated numerical control code) that the image analyzer detected from the printed layer and/or prior layers. Based on AIFC from other printed jobs, image analyzer 180 can determine whether any adjustments should be made to the print parameters of the next or subsequent layers of the partially printed object to achieve the desired mechanical, optical and/or electrical properties in view of the detected anomalies. For example, if, based on the detected anomalies, image analyzer 180 determines for a current and/or prior layers of a partially printed object that the mechanical properties for the completed printed object would be weaker than desired, then image analyzer 180 can instruct numerical control code generator 110 and/or control module 160 to adjust certain print parameters (e.g., increase infill density and/or change the infill pattern) on the next or any subsequent layers so that the desired mechanical properties can be achieved.

In some embodiments, operations 610-680 are repeated for each layer, or for any number of layers, that are deposited for a printed object. Image analyzer 180 can use the data obtained at each layer, as well as AIFC from other print jobs to modify the print parameters for the next and/or subsequent layers to achieve the desired mechanical, optical and/or electrical properties and/or the desired design of the printed object. In further embodiments, the mechanical, optical and/or electrical properties of the completed printed object can be measured.

The division of when the particular portions of process 600 are performed can vary, and no division or a different division is within the scope of the subject matter disclosed herein. Note that, in some embodiments, blocks of process 600 can be performed at any suitable times. It should be understood that at least some of the portions of process 600 described herein can be performed in any order or sequence not limited to the order and sequence shown in and described in connection FIG. 6 in some embodiments. Also, some portions of process 600 described herein can be performed substantially simultaneously where appropriate or in parallel in some embodiments. Additionally or alternatively, some portions of process 600 can be omitted in some embodiments.

Process 600 can be implemented in any suitable hardware and/or software. For example, in some embodiments, process 600 can be implemented in image analyzer 180 or numerical control code generator 110.

In some embodiments, image analyzer 180 can learn anomaly patterns for each layer of a printed object in order to enable image analyzer 180 to adaptively adjust print parameters at the layer level during the printing process (e.g., as described in connection with FIG. 6) for similar or different objects to achieve desired mechanical, optical and/or electrical properties.

Certain print parameters impact the mechanical, optical and/or electrical properties of a printed object. For example, infill density and infill patterns can impact mechanical properties like maximum tensile strength ($R_m$), yield strength ($Rp_{2\%}$), elongation at break ($A_{0\%}$), Young's modulus (E), fatigue ($\sigma_d$), Poisson's ratio, mass and specific gravity.

To understand how anomaly patterns and certain print parameters actually impact the mechanical, optical and/or electrical properties of a printed object, an object can be printed numerous times, while varying the print parameters which have an impact on the mechanical, optical and/or electrical properties of a printed object. The anomaly pattern for each printed object can be determined and recorded at the layer level as described, for example, in connection with FIG. 6 (e.g., at 670). In addition, the mechanical, optical and/or electrical properties of each printed object can be measured and recorded.

Figure 8:
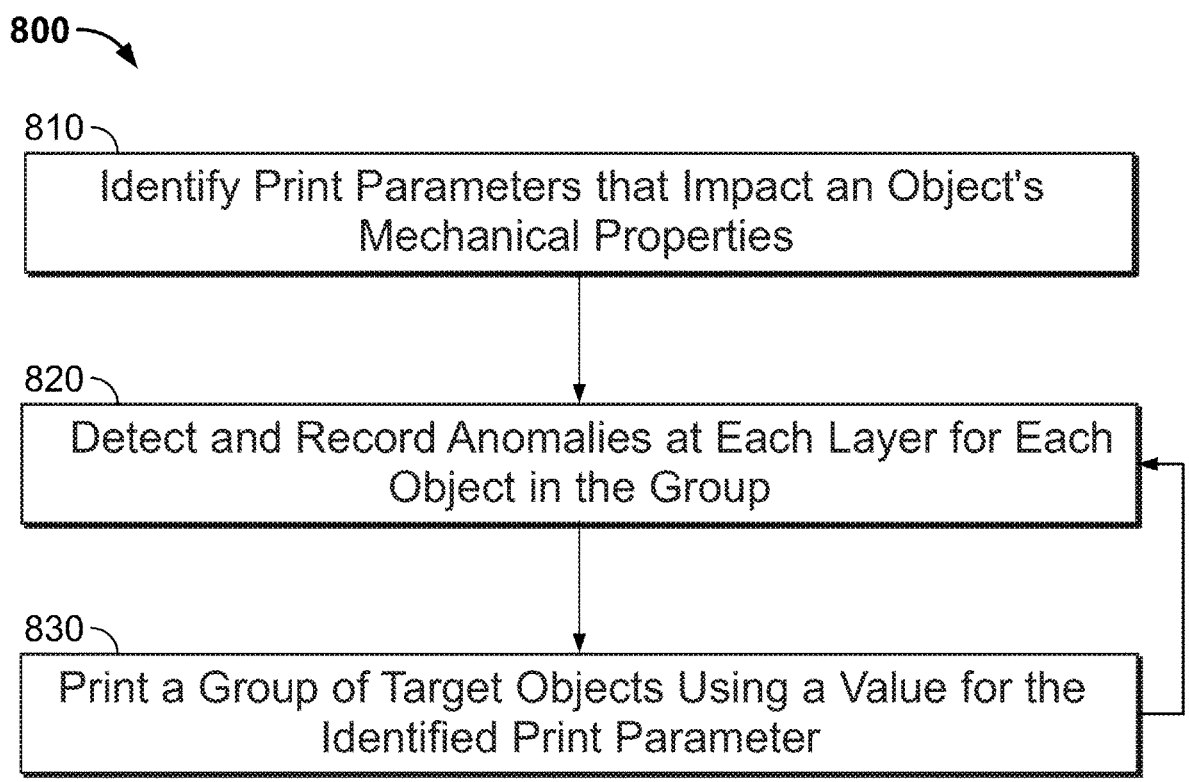
FIG. 8 is an example of a training process for learning anomaly patterns and anomaly rates based on different infill density and infill patterns and how those anomaly patterns and anomaly rates affect the printed object's mechanical properties in accordance with some embodiments.

FIG. 8 shows, an example 800 of a training process for learning anomaly patterns and anomaly rates based on different infill density and infill patterns and how those anomaly patterns and anomaly rates affect the printed object's mechanical properties, in accordance with some embodiments.

At 810, one or more print parameters can be identified that impact an object's mechanical properties. For example, infill density and infill pattern can be identified as impacting an object's mechanical properties. In some embodiments, artificial intelligence algorithms can be used to identify other print parameters that impact an object's mechanical properties.

At 820, a predetermined number ("a group") of a target object can be printed and one or more print parameters that have been identified to impact the target object's mechanical properties can be kept the same for the entire group. For example, each object in the group, can be printed specifying the same infill pattern and infill density print parameters.

At 830, anomalies can be detected and recorded at a layer level for each printed object in the group, as described in connection with 670 of FIG. 6. For example, differences between an actual print path and a print path extracted from the generated control code can be determined for each layer. After each target object in the group is printed, the mechanical properties for that target object can be measured and recorded.

After 830, process 800 can loop back to 820 and, another predetermined number of the target object can be printed at different infill density and/or infill pattern.

820 and 830 can be repeated as many times as necessary to train image analyzer 180 to learn how anomaly patterns and different identified print parameters (e.g., infill density and infill pattern) affect the mechanical properties of an object. Each time a predetermined number of the target object is printed ("a group") the identified parameter (e.g., infill density and/or infill pattern) can be changed. The table below reflects example groups for a target object and their specified infill density and infill pattern print parameters:

| Target Object | Infill Density | Infill Pattern |
|---|---|---|
| Group 1 | 100% | Solid |
| Group 2 | 85% | Honeycomb |
| Group 3 | 85% | Triangular |
| Group 4 | 50% | Honeycomb |
| Group 5 | 50% | Triangular |
| Group 6 | 20% | Honeycomb |
| Group 7 | 20% | Triangular |

In some embodiments, the infill density and infill pattern print parameters are held constant for each layer of a printed object. In other embodiments, the infill density and/or infill pattern is varied for different layers of an object depending where the layer is located or at random.

Once image analyzer 180 has learned how different anomaly rates and patterns and the identified print parameters (e.g., different infill density and infill patterns) affect the mechanical properties of an object, the image analyzer can adaptively adjust the values for the identified print parameters during a print job (e.g., at a layer level) to achieve desired mechanical properties. For example, image analyzer 180 can detect that printed layers of a partially printed object have a certain anomaly rate and pattern that would likely result in sub-par mechanical properties for the printed object once completed if the infill density and infill pattern were not adjusted. Image analyzer 180 can then adjust the infill rate and infill pattern print parameters for the next and/or any subsequent layers to achieve the desired mechanical properties, while also trying to reduce the occurrence of anomalies.

A similar process can be performed for learning how anomaly patterns affect optical and/or electrical properties of an object. For example, print parameters that impact the optical and/or electrical properties of an object can be identified. Groups of a target object can be printed, controlling the identified print parameters across the groups of a target object as described above. Once image analyzer 180 has learned how different anomaly rates and patterns and the identified print parameters affect the electrical and/or optical properties of an object, the image analyzer can adaptively adjust values for the identified print parameters during a print job, at a layer level, to achieve desired electrical and/or optical properties.

A similar process can be performed for learning how non-controllable variables (i.e., variable that are non-controllable without human intervention) affect mechanical, optical and/or electrical properties of an object. For example, non-controllable variables that impact the mechanical, optical and/or electrical properties of an object can be identified. Groups of a target object can be printed, controlling the identified non-controllable variable across the groups of a target object as described above. Once image analyzer 180 has learned how different anomaly rates and patterns and the identified print non-controllable variables affect the mechanical, electrical and/or optical properties of an object, the image analyzer can adaptively adjust values for print parameters during a print job, at a layer level, to compensate for the non-controllable variables and to achieve desired electrical and/or optical properties.

The division of when the particular portions of process 800 are performed can vary, and no division or a different division is within the scope of the subject matter disclosed herein. Note that, in some embodiments, blocks of process 800 can be performed at any suitable times. It should be understood that at least some of the portions of process 800 described herein can be performed in any order or sequence not limited to the order and sequence shown in and described in connection FIG. 8 in some embodiments. Also, some portions of process 800 described herein can be performed substantially simultaneously where appropriate or in parallel in some embodiments. Additionally or alternatively, some portions of process 800 can be omitted in some embodiments.

Process 800 can be implemented in any suitable hardware and/or software. For example, in some embodiments, process 800 can be implemented in image analyzer 180 or numerical control code generator 110.

In some embodiments, image analyzer 180 can use generated topographical images, and/or other generated images for the printed layer (as described in 660 of FIG. 6), as well as the generated numerical control code for the printed layer, to learn the relationship between the print parameters and the resulting print head motion, as well as the anomalies (e.g., unintended gaps or curled edges, warped or uneven patterns, points of excessive extrusion, curled edges, deviations from the print path specified in the numerical control code, unintended thread-like or other foreign artifact and/or any other disruption in the printed layer) in the extruded layer. Image analyzer 180 can also invert the learned relationship to calculate the optimal numerical control code input parameters that will result in a desired print head motion and minimize anomalies in the extruded layer. More specifically, input variables to the artificial intelligence algorithms can include: the previous measured position of the printer head (represented by $\hat{x}_{i-1}$); the control code print parameters that resulted in the previous position of the print head (represented by $\theta_{i-1}$); and the current measure position of a printer head (represented by And the output variable can be the numerical control code parameters that resulted in the current position of the printer head (represented by $\theta$). Together the input variables and the output variable can serve as a single training sample for the artificial intelligence algorithms. A single printed layer can result in hundreds of such training samples. These training samples, along with knowledge of anomalies in prior layers, the desired specifications of the production design, the print features of the additive manufacturing printer and/or ambient conditions can be used to calculate the optimal print parameters to generate a desired print head motion. In some embodiments, training samples, along with knowledge of anomalies in prior layers, the desired specifications of the production design, the features of the additive manufacturing printer and/or ambient conditions can be used to calculate the optimal print parameters, as well as the optimum placement of X-Y-Z setpoints and instructions for the print path, in subsequent layers.

In some embodiments, image analyzer 180 can also be applied to learn the relationship between print parameters and overall characteristics of a layer. For example, image analyzer 180 can be applied to learn a total number of anomalies in an extruded layer, how closely motion of the print head and/or build plate resembled print path instructions in generated numerical control code, and specified infill density. In some embodiments, image analyzer 180 can invert learned relationships to calculate print parameters that will result in a layer that most closely resembles specifications of a production design, including desired mechanical, optical and/or electrical properties.

In some embodiments, image analyzer 180 can use generated topographical images, and/or other generated images, for a printed layer, as well as generated numerical control code for the printed layer, to learn a relationship between non-controllable variables (i.e., variable that are non-controllable without human intervention) and the resulting print head motion, as well as the anomalies (e.g., unintended gaps or curled edges, warped or uneven patterns, points of excessive extrusion, deviations from the print path specified in the numerical control code, unintended thread-like or other foreign artifacts and/or any other disruption in the printed layer) in a deposited layer. If image analyzer 180 discovers that non-controllable variables are adversely affecting, beyond a threshold tolerance, a resulting print head motion and/or anomalies in a deposited layer, image analyzer 180 can send an alert to control module 160. Control module 160, upon receipt of an alert, can display a warning on a display of additive manufacturing system 100 and/or alert an operator via email, text or any other suitable electronic mechanism. In some embodiments, image analyzer 180 can be configured to alert an operator directly via email, text or any other suitable electronic mechanism. For example, in some embodiments, if image analyzer 180 determines that ambient humidity, temperature and/or light is negatively impacting a resulting print head motion or the number of anomalies in a layer is beyond a predetermined tolerance, then image analyzer 180 can send an alert to control module 160 and/or an operator. In some embodiments, if image analyzer 180 determines that wear and tear of additive manufacturing printer 115 and/or the total amount of filament available to print head 140 (e.g., low amount of filament) is negatively impacting a resulting print head motion or the number of anomalies in a layer is beyond a predetermined tolerance, then image analyzer 180 can send an alert to control module 160 and/or an operator to replace the additive manufacturing printer and/or to refill the filament. In some embodiments, if image analyzer 180 determines that a voltage variation is negatively impacting a resulting print head motion or the number of anomalies in a layer is beyond a predetermined tolerance, then image analyzer 180 can send an alert to control module 160 and/or an operator to check a voltage source.

In some embodiments, any suitable computer readable media can be used for storing instructions for performing the functions and/or processes described herein. For example, in some embodiments, computer readable media can be transitory or non-transitory. For example, non-transitory computer readable media can include media such as non-transitory magnetic media (such as hard disks, floppy disks, etc.), non-transitory optical media (such as compact discs, digital video discs, Blu-ray discs, etc.), non-transitory semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, and any suitable media that is fleeting and devoid of any semblance of permanence during transmission, and/or any suitable intangible media.

The provision of the examples described herein (as well as clauses phrased as "such as," "e.g.," "including," and the like) should not be interpreted as limiting the claimed subject matter to the specific examples; rather, the examples are intended to illustrate only some of many possible aspects. It should also be noted that, as used herein, the term mechanism can encompass hardware, software, firmware, or any suitable combination thereof.

The additive manufacturing system and method have been described in detail with specific reference to these illustrated embodiments. It will be apparent, however, that various modifications and changes can be made within the spirit and scope of the disclosure as described in the foregoing specification, and such modifications and changes are to be considered equivalents and part of this disclosure. The scope of the invention is limited only by the claims that follow.

What is claimed is:

1. An additive manufacturing system, comprising:
    a print head that is configured to print an object in a layer by layer manner;
    an illumination source for providing illumination to a surface of a printed layer of the object;
    an image sensor configured to capture an image of the printed layer; and
    at least one hardware processor configured to:
        receive a captured image;
        obtain one or more desired mechanical properties for the object;
        generate a three-dimensional topographical image of the printed layer;
        identify an anomaly in the printed layer from the generated topographical image using a first artificial intelligence algorithm that is configured to detect anomalies in printed layers;
        determine a correlation between the identified anomaly and one of an infill density and an infill pattern used to print the printed layer using a second artificial intelligence algorithm that is configured to determine correlations between identified anomalies and the one of the infill density and the infill pattern;
        adjust a value for the one of the infill density and the infill pattern to be used by the print head to print a subsequent layer of the object; and
        cause the print head to print the subsequent layer of the object using the value for the one of the infill density and the infill pattern to substantially achieve the one or more desired mechanical properties.

2. The additive manufacturing system of claim 1, wherein the three-dimensional topographical image of the printed layer is generated using one of a shape-from-focus algorithm, a shape-from-shading focus algorithm, a photometric stereo algorithm, and a Fourier ptychography modulation algorithm.

3. The additive manufacturing system of claim 1, wherein at least one of the first artificial intelligence algorithm and the second artificial intelligence algorithm includes at least one of machine learning, hidden Markov models, recurrent neural networks, convolutional neural networks, Bayesian symbolic methods, support vector machines, and general adversarial network.

4. The additive manufacturing system of claim 1, wherein identifying the anomaly is performed by comparing the generated three-dimensional topographical image with at least one of: generated numerical control code for the printed layer, one or more prior layers of the printed object, or a production design for the printed object.

5. The additive manufacturing system of claim 1, wherein the at least one hardware processor is further configured to:
identify a print parameter that affects at least one of a mechanical property, an optical property, and an electrical property of the object;
measure the at least one of the mechanical property, the optical property, and the electrical property after the object is printed;
determine at least one of an anomaly rate and an anomaly pattern of the object; and
determine how the at least one the anomaly rate and the anomaly pattern and the print parameter impact the at least one of the mechanical property, the optical property, and the electrical property of the object.

6. The additive manufacturing system of claim 5, wherein identifying a print parameter uses an artificial intelligence algorithm.

7. The additive manufacturing system of claim 5, wherein determining how the at least one the anomaly rate and the anomaly pattern and the print parameter impact the at least one of the mechanical property, the optical property, and the electrical property uses an artificial intelligence algorithm.

8. A method for additive manufacturing, comprising:
receiving a captured image produced by an image sensor configured to capture an image of a printed layer of an object printed in a layer by layer manner;
obtaining one or more desired mechanical properties for the object;
generating a three-dimensional topographical image of the printed layer using a hardware processor;
identifying an anomaly in the printed layer from the generated topographical image using a first artificial intelligence algorithm that is configured to detect anomalies in printed layers;
determining a correlation between the identified anomaly and one of an infill density and an infill pattern used to print the printed layer using a second artificial intelligence algorithm that is configured to determine correlations between identified anomalies and the one of the infill density and the infill pattern;
adjusting a value for the one of the infill density and the infill pattern to be used by the print head to print a subsequent layer of the object; and
causing the print head to print the subsequent layer of the object using the value for the one of the infill density and the infill pattern to substantially achieve the one or more desired mechanical properties.

9. The method of claim 8, wherein the three-dimensional topographical image of the printed layer is generated using one of a shape-from-focus algorithm, a shape-from-shading focus algorithm, a photometric stereo algorithm, and a Fourier ptychography modulation algorithm.

10. The method of claim 8, wherein at least one of the first artificial intelligence algorithm and the second artificial intelligence algorithm includes at least one of machine learning, hidden Markov models, recurrent neural networks, convolutional neural networks, Bayesian symbolic methods, support vector machines, and general adversarial network.

11. The method of claim 8, wherein identifying the anomaly is performed by comparing the generated three-dimensional topographical image with at least one of: generated numerical control code for the printed layer, one or more prior layers of the printed object, and a production design for the printed object.

12. The method of claim 8, further comprising:
identifying a print parameter that affects at least one of a mechanical property, an optical property, and an electrical property of the object;
measuring the at least one of the mechanical property, the optical property, and the electrical property after the object is printed;
determining at least one of an anomaly rate and an anomaly pattern of the object; and
determining how the at least one the anomaly rate and the anomaly pattern and the print parameter impact the at least one of the mechanical property, the optical property, and the electrical property of the object.

13. The method of claim 12, wherein identifying a print parameter uses an artificial intelligence algorithm.

14. The method of claim 12, wherein determining how the at least one of the anomaly rate and the anomaly pattern and the print parameter impact the at least one of the mechanical property, the optical property, and the electrical property of the object uses an artificial intelligence algorithm.

15. A non-transitory computer-readable medium containing computer-executable instructions that, when executed by a processor, cause the processor to perform a method for additive manufacturing comprising:
receiving a captured image produced by an image sensor configured to capture an image of a printed layer of an object printed in a layer by layer manner;
obtaining one or more desired mechanical properties for the object;
generating a three-dimensional topographical image of the printed layer;
identifying an anomaly in the printed layer from the generated topographical image using a first artificial intelligence algorithm that is configured to detect anomalies in printed layers;
determining a correlation between the identified anomaly and one of an infill density and an infill pattern used to print the printed layer using a second artificial intelligence algorithm that is configured to determine correlations between identified anomalies and the one of the infill density and the infill pattern;
adjusting a value for the one of the infill density and the infill pattern to be used by the print head to print a subsequent layer of the object; and
causing the print head to print the subsequent layer of the object using the value for the one of the infill density and the infill pattern to substantially achieve the one or more desired mechanical properties.

16. The non-transitory computer-readable medium of claim 15, wherein the three-dimensional topographical image of the printed layer is generated using one of a shape-from-focus algorithm, a shape-from-shading focus algorithm, a photometric stereo algorithm, and a Fourier ptychography modulation algorithm.

17. The non-transitory computer-readable medium of claim 15, wherein at least one of the first artificial intelligence algorithm and the second artificial intelligence algorithm includes at least one of machine learning, hidden Markov models, recurrent neural networks, convolutional neural networks, Bayesian symbolic methods, support vector machines, and general adversarial network.

18. The non-transitory computer-readable medium of claim 15, wherein identifying the anomaly is performed by comparing the generated three-dimensional topographical image with at least one of: generated numerical control code for the printed layer, one or more prior layers of the printed object, and a production design for the printed object.

19. The non-transitory computer-readable medium of claim 15, wherein the method further comprises:

identifying a print parameter that affects at least one of a mechanical property, an optical property, and an electrical property of the object;

measuring the at least one of the mechanical property, the optical property, and the electrical property after the object is printed;

determining at least one of an anomaly rate and an anomaly pattern of the object; and determining how the at least one the anomaly rate and the anomaly pattern and the print parameter impact the at least one of the mechanical property, the optical property, and the electrical property of the object.

20. The non-transitory computer-readable medium of claim 19, wherein identifying a print parameter uses an artificial intelligence algorithm.

21. The non-transitory computer-readable medium of claim 19, wherein determining how the at least one of the anomaly rate and the anomaly pattern and the print parameter impact the at least one of the mechanical property, the optical property, and the electrical property of the object uses an artificial intelligence algorithm.

* * * * *